United States Patent
Kruspe et al.

(10) Patent No.: US 7,405,563 B2
(45) Date of Patent: Jul. 29, 2008

(54) COMPENSATION OF MAGNETIC INFLUENCE IN A MWD SYSTEM

(75) Inventors: Thomas Kruspe, Niedersachsen (DE); Volker Krueger, Celle (DE); Martin Blanz, Celle (DE); Roland E. Chemali, Kingwood, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/676,462

(22) Filed: Feb. 19, 2007

(65) Prior Publication Data

US 2007/0206555 A1 Sep. 6, 2007

Related U.S. Application Data

(60) Provisional application No. 60/774,699, filed on Feb. 17, 2006.

(51) Int. Cl.
  *G01V 3/00* (2006.01)
(52) U.S. Cl. .................. 324/303; 324/300
(58) Field of Classification Search ........ 324/303, 324/300, 338–343; 702/6, 9, 10; 367/37, 367/47, 38; 250/254; 73/151
See application file for complete search history.

(56) References Cited

U.S. PATENT DOCUMENTS

| | | | |
|---|---|---|---|
| 4,350,955 A | 9/1982 | Jackson et al. ............ 324/303 |
| 5,397,893 A | 3/1995 | Minette ............ 250/254 |
| 5,513,528 A | 5/1996 | Holenka et al. ............ 73/151 |
| 5,623,407 A | 4/1997 | Brooks ............ 364/422 |
| 6,047,237 A * | 4/2000 | Michmerhuizen ........... 701/224 |
| 6,111,408 A | 8/2000 | Blades et al. ............ 324/303 |
| 6,326,785 B1 * | 12/2001 | Kruspe ............ 324/303 |
| 6,966,211 B2 | 11/2005 | Wu ............ 73/1.75 |
| 2004/0124837 A1 | 7/2004 | Prammer et al. ........... 324/303 |
| 2006/0273787 A1 * | 12/2006 | Blanz ............ 324/303 |

FOREIGN PATENT DOCUMENTS

| | | |
|---|---|---|
| EP | 0687919 A1 | 12/1995 |
| WO | WO99/32897 | 7/1999 |

OTHER PUBLICATIONS

R. Bittner et al.; *Magnetic Resonance While Drilling—A Quantum Leap in Everyday Petrophysics*, SPE 100336, SPE Europec/EAGE Annual Conference and Exhibition, Vienna, Austria, Jun. 12-15, 2006, pp. 1-7.

* cited by examiner

*Primary Examiner*—Brij B Shrivastav
(74) *Attorney, Agent, or Firm*—Madan, Mossman & Sriram, P.C.

(57) ABSTRACT

The present disclosure provides a downhole tool that includes a magnetometer and a nuclear magnetic resonance (NMR) sensor. One or more compensating magnets are provided on the tool to cancel or offset the effect of the magnetic field of the magnets of the NMR sensor on the magnetometer measurements made during drilling of a wellbore. The compensating magnets may have the same magnetic field characteristics as the sensor magnets and may be made of the same material.

25 Claims, 4 Drawing Sheets

COMPENSATION OF MAGNETIC INFLUENCE IN A MWD SYSTEM

CROSS-REFERENCES TO RELATED APPLICATIONS

This application claims priority from U.S. Provisional Patent Application Ser. No. 60/774,699 filed on 17 Feb. 2006.

BACKGROUND OF THE INVENTION

1. Field of the Invention

The invention relates generally to downhole formation analysis and in particular to the compensation of measurements made by a magnetometer during measurement while drilling.

2. Summary of the Related Art

Oil well logging has been known for many years and provides information about various characteristics of the particular earth formation being drilled. In conventional oil well logging, after a well or borehole has been drilled, a probe known as a sonde is lowered into the borehole to determine characteristics of the formations which the well has traversed. The probe is typically a hermetically sealed cylindrical body which hangs at the end of a long cable which gives mechanical support to the sonde and provides power to various sensors and other instrumentation inside the sonde. The cable also provides communication channels for transferring information between the sonde and surface equipment. The sonde is typically pulled while the various sensors in the sonde take measurements, which are processed to determine the various characteristics of the formation. It thus becomes possible to measure parameters or characteristics of the earth's formations as a function of depth, that is, while the sonde is being pulled uphole. Although, such "wireline" measurements are normally made in real time, these measurements, however, are taken long after the actual drilling of the well.

There are also several teachings in prior art for taking measurements of formation parameters while the borehole is being drilled, i.e. while drilling the wellbore. For example, U.S. Pat. No. 5,397,893 to Minette, discloses a method for analyzing data from a measurement-while-drilling (MWD) formation evaluation logging tool which compensates for the rotation of the logging tool (along with the rest of the drillstring) during measurement periods. U.S. Pat. No. 5,513,528 to Holenka et al. (the "'528 patent") discloses a method and apparatus for measuring formation characteristics as a function of azimuth about the borehole. The measurement apparatus of the '528 patent includes a logging while drilling tool which rotates in the borehole during drilling of the wellbores. In the '528 patent tool, the down vector of the tool is derived first by determining an angle "N" between a vector to the earth's north magnetic pole, as referenced to the cross sectional plane of the measuring while drilling (MWD) tool and a gravity down vector as referenced in the plane. The tool includes magnetometers and accelerometers placed orthogonally in a cross-sectional plane. Using the magnetometers and/or accelerometer measurements, the toolface angle can be determined. The angle N is transmitted to the tool, thereby allowing a continuous determination of the gravity down position in the logging while drilling tool Neither Minette nor Holenka address possible sources of error in relying on readings made using magnetometers on a rotating drillstring. There are prior art methods that address the problem of correction of errors caused by metallic drill collars, casing, and accumulated debris. For example, U.S. patent application Ser. No. 11/256,794 of Blanz addresses the affect on magnetometer readings due to the rotation of the drillstring. U.S. Pat. No. 5,623,407 to Brooks discloses correction of bias errors due to interference and other sources by choosing the biases that minimize the variance of magnetic field magnitude at several sensor orientations. U.S. Pat. No. 6,966,211 to Wu discloses a method to correct errors in bias, scale-factor, misalignment of cross-axial magnetometers, and bias or scale-factor of axial magnetometer by requiring the magnitude of measured cross-axial magnetic field to be as constant as possible over several tool face angles at a survey point in a wellbore and the magnitude of the measured total magnetic field and dip angle equal to the reference values, respectively.

In general, the correction methods described above work reasonably well when the magnetometer is at a sufficiently large distance from magnetic disturbances on the downhole assembly. However, when a nuclear magnetic resonance (NMR) sensor is used in the tool, there is a major disturbance to the earth's magnetic field due to the magnets that are used for making the measurements. Typically, the magnets used in the NMR sensor are strong permanent magnets. For example, U.S. Pat. No. 6,111,408 to Blades discusses NMR measurements made utilizing permanent magnets with a field of 47 mT (470 Gauss). In contrast, the earth's magnetic field is of the order of half a Gauss. Even though the field of the magnets used for NMR measurements decays with distance, the disturbance to the earth's magnetic field can be significant to adversely affect the magnetometer measurements. The present invention provides apparatus and method that addresses this problem.

SUMMARY OF THE INVENTION

The present disclosure, in one aspect, provides an apparatus configured to correct for an effect of a source of a magnetic disturbance on a downhole assembly conveyed in a borehole in the earth formation. The apparatus includes at least one magnet on the downhole assembly configured to produce a magnetic field at a selected location on the downhole assembly that substantially cancels a magnetic field produced by the source of the magnetic disturbance. The at least one magnet is further configured so that a gradient of the magnetic field produced by the at least one magnet substantially cancels a gradient of the magnetic field produced by the source of the disturbance. The at least one magnet may include a pair of magnets disposed on opposite sides of the selected location, each of the pair of magnets having a similar orientation. The source of the magnetic disturbance may be a magnet of a nuclear magnetic resonance sensor, the magnet of the NMR sensor being made of substantially the same material as a material of the at least one magnet. The material of the at least one magnet may be selected to maintain cancellation of the field produced by the source of magnetic disturbance when a temperature of the downhole assembly changes. The downhole assembly may be a bottomhole assembly conveyed on a drilling tubular or a logging string conveyed on a wireline.

The disclosure also teaches a method of correcting for an effect of a source of the magnetic disturbance on a downhole assembly conveyed in a borehole in the earth formation. The method includes positioning at least one magnet on the downhole assembly on a side opposite to the source of the magnetic disturbance from a selected location on the downhole assembly and producing a magnetic field at the selected location that substantially cancels a magnetic field produced by the source of the magnetic disturbance, and a gradient of the magnetic field produced by the at least one magnet substantially cancels a gradient of the magnetic field produced by the source of the disturbance. Positioning the at least one magnet may include positioning a pair of magnets on opposite sides of the selected location, each of the pair of magnets having a similar orientation. The source of the magnetic disturbance may be a day magnetic of the nuclear magnetic resonance sensor and the method may further include using a material for the at least one magnet that is substantially the same as the magnet of the NMR sensor. The downhole assembly may include or logging string and the method may further include conveying the logging string into the borehole on a wireline. The downhole assembly may be at bottomhole assembly, and a method may further include conveying the BHA into the borehole on a drilling tubular.

Another embodiment of the disclosure is an apparatus for evaluating an earth formation. The apparatus includes a downhole assembly conveyed in a borehole in the earth formation in a source of a magnetic disturbance on the downhole assembly. A magnetometer on the downhole assembly is configured to provide a measurement indicative of an orientation of the downhole assembly, the measurement being subject to the magnetic disturbance. At least one magnet on the downhole assembly is configured to produce a magnetic field at a location of the magnetometer that substantially cancels a magnetic field produced by the source of the magnetic disturbance, the at least one magnet is further configured so that a gradient of the magnetic field produced by the at least one magnet substantially cancels a gradient of the magnetic field produced by the source of the disturbance. A formation evaluation sensor on the downhole assembly is configured to provide an FE measurement indicative of a property of the of the earth formation. A processor is configured to associate an orientation angle with the FE measurement using the output of the magnetometer. The at least one magnet may include bit of magnets disposed on opposite sides of a selected location, each of the pair of magnets having a similar orientation. The source of the magnetic disturbance may be a magnet of a nuclear magnetic resonance sensor, the magnetic of the NMR sensor being made of substantially the same material as a material of the at least one magnet. The Machida of the at least one magnet may be selected to maintain the cancellation in the presence of the temperature change of the downhole assembly. The downhole assembly may be a bottomhole assembly conveyed on a drilling tubular or it may be a logging string conveyed on a wireline. The processor may further be configured to store of the formation evaluation measurement and the associated orientation on a suitable medium and/of display the FE measurement and the associated orientation. The FE sensor may be a resistivity sensor, an acoustic sensor, a density sensor and/or a porosity sensor.

Another embodiment of the disclosure is a method of evaluating an earth formation. The method includes conveying a downhole assembly in a borehole in the earth formation, providing a magnetic disturbance on the downhole assembly using a source thereof, using a magnetometer on the downhole assembly to provide a measurement indicative of an orientation of the downhole assembly, the measurement being subject to the magnetic disturbance, using at least one magnet on the downhole assembly to produce a magnetic field at a location of the magnetometer that substantially cancels a magnetic field produced by the soles of the magnetic disturbance and substantially cancels ingredient of the magnetic field by the source of the disturbance. The method further includes making a formation evaluation measurement indicative of a property of the formation, and associating an orientation angle with the formation evaluation measurement using the output of the magnetometer. The method may further include using, for the at least one magnet, a pair of magnets disposed on opposite sides of the magnetometer, each of the pair of magnets having a similar orientation. The method may further include using, as the source of the magnetic disturbance, a magnet of a nuclear magnetic resonance sensor, the material of the magnets of the NMR sensor being substantially the same has a material of the at least one magnet. The method may further include conveying the downhole assembly on a drilling tubular or a wireline. The method may further include storing the formation evaluation measurement and the associated orientation on a suitable medium and/or displaying the formation evaluation measurement and the associated orientation. The method may further include using, as the FE sensor, a resistivity sensor, an acoustic sensor, a density sensor and/or a porosity sensor.

BRIEF DESCRIPTION OF THE FIGURES

For detailed understanding of the present disclosure, references should be made to the following detailed description of exemplary embodiment(s), taken in conjunction with the accompanying drawings, in which like elements have been given like numerals, wherein.

DETAILED DESCRIPTION OF THE EMBODIMENTS

In view of the above, the present invention through one or more of its various aspects and/or embodiments is presented to provide one or more advantages, such as those noted below.

Figure 1:
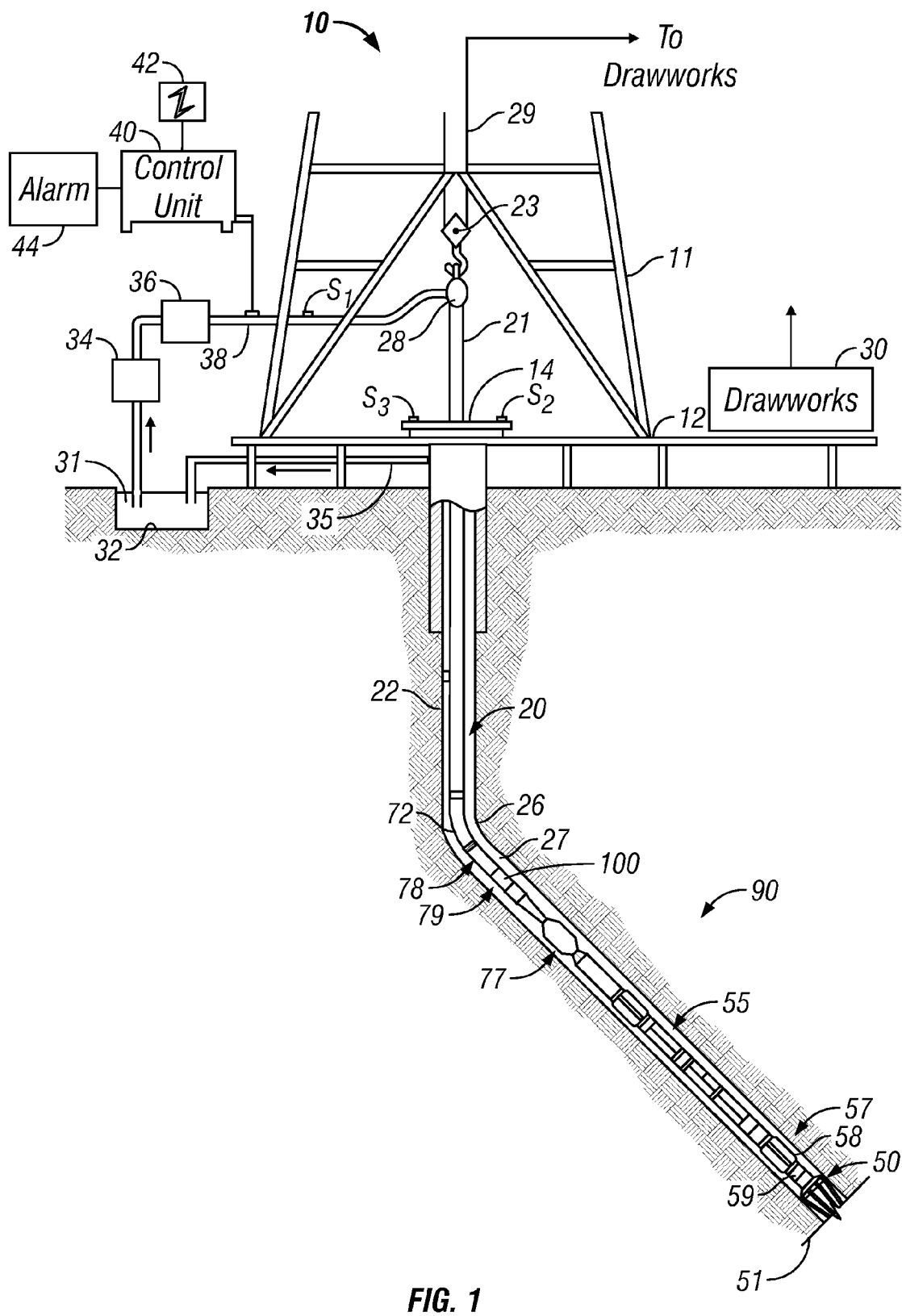
FIG. 1 is an illustration of a downhole bottomhole assembly (BHA) deployed in a borehole from a tubing that includes the apparatus according to one embodiment of the present invention.

FIG. 1 illustrates a schematic diagram of an MWD drilling system 10 with a drill string 20 carrying a drilling assembly 90 (also referred to as the bottom hole assembly, or "BHA") conveyed in a "wellbore" or "borehole" 26 for drilling the wellbore. A compensating magnetic assembly or (demagnetizing sub was the object of another disclosure for eliminating the magnetism from iron or other filings particles in the mud). 100 is positioned on the drill string 20 below an NMR sensor or tool 78. The drilling system 10 includes a conventional derrick 11 erected on a floor 12 which supports a rotary table 14 that is rotated by a prime mover such as an electric motor (not shown) at a desired rotational speed. The drill string 20 includes tubing such as a drill pipe 22 or a coiled-tubing extending downward from the surface into the borehole 26. The drill string 20 is pushed into the wellbore 26 when a drill pipe 22 is used as the tubing. For coiled-tubing applications, a tubing injector (not shown), however, is used to move the tubing from a source thereof, such as a reel (not shown), into the wellbore 26. The drill bit 50 attached to the end of the drill string 20 breaks up the geological formations when it is rotated to drill the borehole 26. If a drill pipe 22 is used, the drill string 20 is coupled to a drawworks 30 via a Kelly joint 21, swivel 28 and line 29 through a pulley 23. During drilling operations, the drawworks 30 is operated to control the weight on bit, a parameter that affects the rate of penetration.

The operation of the drawworks is well known in the art and is thus not described in detail herein.

During drilling operations, a suitable drilling fluid 31 from a mud pit (source) 32 is circulated under pressure through a channel in the drill string 20 by a mud pump 34. The drilling fluid passes from the mud pump 34 into the drill string 20 via a desurger 36, fluid line 38 and Kelly joint 21. The drilling fluid 31 is discharged at the borehole bottom 51 through openings in the drill bit 50. The drilling fluid 31 circulates uphole through the annular space 27 between the drill string 20 and the borehole 26 and returns to the mud pit 32 via a return line 35. The drilling fluid acts to lubricate the drill bit 50 and to carry borehole cutting or chips away from the drill bit 50. A sensor $S_1$ preferably placed in the line 38 provides information about the fluid flow rate. A surface torque sensor $S_2$ and a sensor $S_3$ associated with the drill string 20 respectively provide information about the torque and rotational speed of the drill string. Additionally, a sensor (not shown) associated with line 29 is used to provide the hook load of the drill string 20.

Rotating the drill pipe 22 rotates the drill bit 50. Also, a downhole motor 55 (mud motor) may be disposed in the drilling assembly 90 to rotate the drill bit 50 and the drill pipe 22 is rotated usually to supplement the rotational power, if required, and to effect changes in the drilling direction.

In the embodiment of FIG. 1, the mud motor 55 is coupled to the drill bit 50 via a drive shaft (not shown) disposed in a bearing assembly 57. The mud motor 55 rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

A drilling sensor module 59 is placed near the drill bit 50. The drilling sensor module 59 contains sensors, circuitry and processing software and algorithms relating to the dynamic drilling parameters. Such parameters may include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module 59 processes the sensor information and transmits it to the surface control unit 40 via the telemetry system 72.

The communication sub 72, a power unit 78 and an NMR tool 79 are all connected in tandem with the drill string 20. Flex subs, for example, are used in connecting the MWD tool 79 in the drilling assembly 90. Such subs and tools form the bottom hole drilling assembly 90 between the drill string 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals may be processed using a downhole processor in the drilling assembly 90.

The surface control unit or processor 40 also receives signals from other downhole sensors and devices, signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 preferably includes a computer or a microprocessor-based processing system, memory for storing programs or models and data, a recorder for recording data, and other peripherals. The control unit 40 is preferably adapted to activate alarms 44 when certain unsafe or undesirable operating conditions occur.

Figure 2:
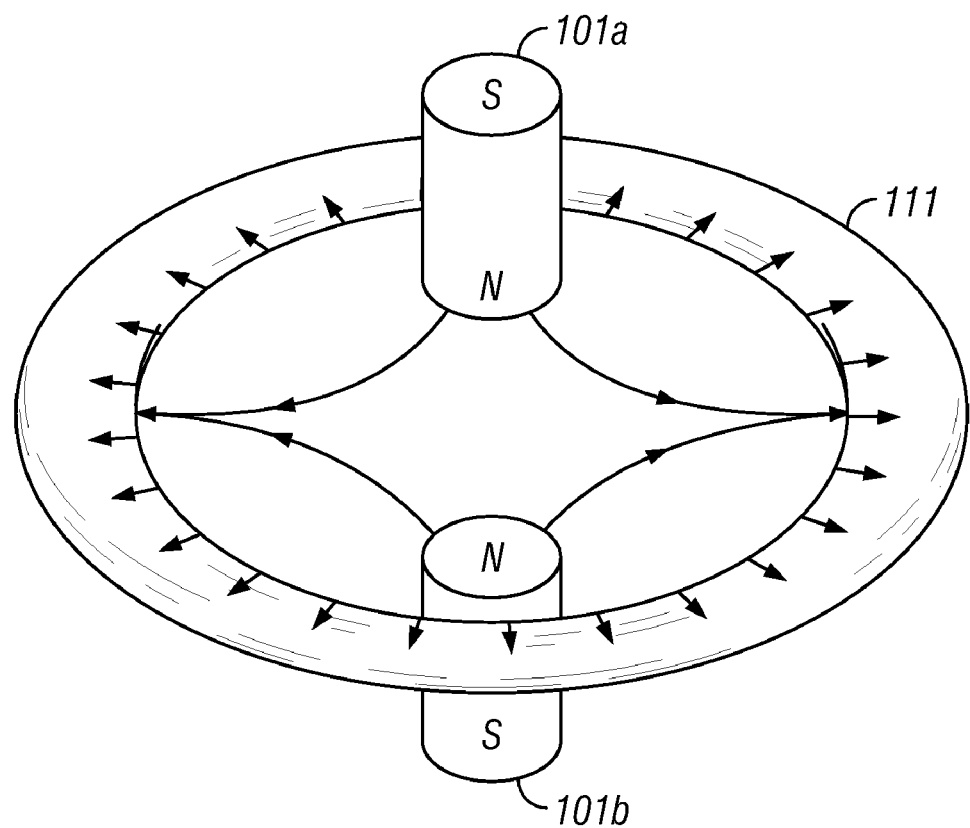
FIG. 2 (prior art) is an illustration of the magnet configuration for an exemplary NMR sensor.

Turning now to FIG. 2 (prior art), the arrangement of magnets for an exemplary NMR sensor for downhole use is shown. Such an arrangement is disclosed, for example, in U.S. Pat. No. 4,350,955 to Jackson. Shown is a pair of permanent magnets with like poles 101a, 101b in an opposed configuration. With such an arrangement, there is a toroidal region 111 in which the magnetic field is uniform and from which spin echo signals can be obtained by pulsing with a radio frequency (RF) magnetic field. As discussed above, the field in the neighborhood of the magnets can be quite large, which can interfere with or affect the measurements made by magnetometers located approximate to the NMR magnets. The particular NMR magnet arrangement of Jackson is only intended for exemplary purposes and is not to be construed as a limitation.

It is common practice to have a magnetometer as part of the BHA which makes measurements of the azimuth of the BHA. The magnetometer measurements are used in the processing of azimuthally sensitive nuclear measurements such as those made by Minette, as well as directional resistivity measurements. The magnetometer reading would then be based on a combination of the earth's field (which gives the azimuth) and the field due to the NMR sensor (which may be regarded as noise). The magnetometer reading will not deliver the correct earth's field. The present invention addresses the errors caused by the NMR sensor by the use of suitably positioned additional magnets.

Figure 3:
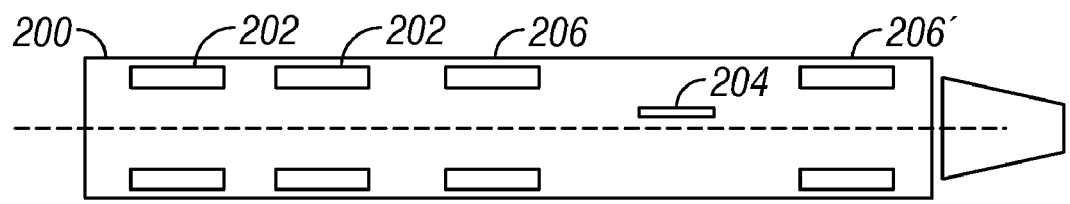
FIG. 3 is a schematic illustration of the disposition of an embodiment of the invention in which compensating magnets are used.

Turning now to FIG. 3, a sub 200 is shown which includes a nuclear magnetic resonance sensor, a magnetometer and a compensating magnet arrangement or an assembly. The permanent magnets of the NMR sensor are depicted by 202. Any suitable magnets may be utilized for the purpose the NMR sensor for the purpose of this invention. For example, the magnets 202 may be solid cylinders as shown in FIG. 2 or may be hollow cylinders in contrast to the solid cylinders as shown in FIG. 2. To simplify the invention the antenna coils used for pulsing the earth formation with RF pulses are not shown in FIG. 3. Exemplary antenna arrangements which may be used for obtaining azimuthal measurements of nuclear spin properties are shown and described in U.S. patent application Ser. No. 10/958,608 of Kruspe et al., assigned to the same assignee of the present application, the contents of which are hereby incorporated in entirety by reference. The sub 200 includes a magnetometer 204. The magnetometer 204 may be a multi-component magnetometer or may comprise three single-component magnetometers. The location of the magnetometer 204 is such that the magnetic field generated by the magnets 202 can adversely affect the recordings or measurements made by the magnetometer 204. Measurements made with the NMR sensor (or other directionally sensitive sensors such as resistivity and gamma ray sensors positioned on the sub 200) are processed by a processor (not shown) in conjunction with the orientation measurements provided by the magnetometer to obtain directional properties of the earth formation. Thus, if the magnetometer readings are incorrect due to the influence of the magnetic field generated by the magnets 202, the processed data will also be incorrect.

Also shown in FIG. 3 is a pair of compensating (bucking) magnets 206, 206'. The compensating magnets 206, in one aspect, may have the same structure as the sensor magnets 202. The compensating magnets 206, 206' may be made of the same material as the sensor magnets 202. When they are made of the same material, then the fields of the sensor magnets and the field of the bucking magnets will be affected in substantially the same manner by temperature changes, and the compensation discussed below will be maintained over a wide range of downhole temperatures. In an alternate embodiment, the material of the bucking magnets is selected to have a coefficient of thermal expansion such that when the temperature changes, the net effect of expansion of be subs, the magnets causing a disturbance, and the bucking magnets maintains the compensation.

Figure 4A:
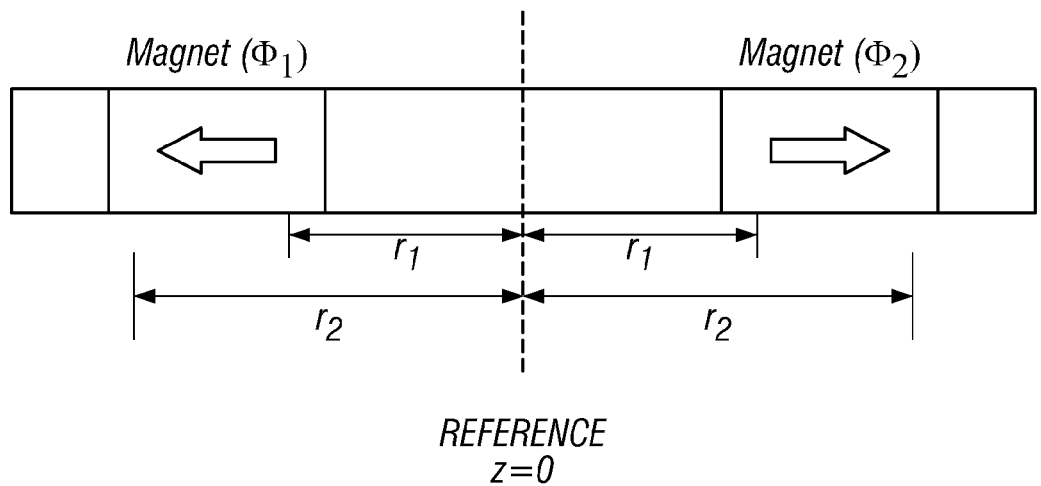
FIGS. 4A and 4B define parameters used for modeling the field for the magnet arrangement of FIG. 3.
Figure 4B:
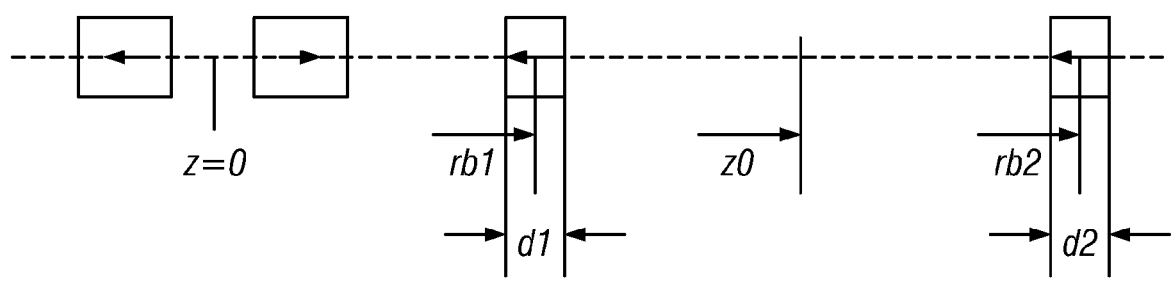

FIGS. 4A and 4B define the parameters that are used for simulating the magnetic field configuration of the magnet arrangement of FIG. 3. As seen in FIG. 4A, the NMR sensor magnets have strengths $\Phi_1$ and $\Phi_2$ and are symmetrically disposed about their center point, which is used as the origin for the modeling. $r_1$ and $r_2$ are assumed distances that poles are away from sensor center position. As seen in FIG. 4B, the magnetometer is at a d in istance $z_0$ from the midpoint of the sensor magnets. It is to be noted that the bucking magnets are magnetized in the same direction. The results given below correspond to different pole strengths for the two bucking magnets of 600 µWb and 300 µWb re on spectively. $r_{b1}$ was taken as 3240 mm, $r_{b2}$ was taken as 6000 mm.

For the modeling results shown below, the pole strength $\Phi$ of the sensor magnets was taken as 15 mWb. The magnetic flux due to the sensor magnets is given by $$B_z(z) = \frac{\Phi}{4\pi\varepsilon^2}\left[\frac{1}{(z+r_2)^2} - \frac{1}{(z+r_1)^2} + \frac{1}{(z-r_2)^2} - \frac{1}{(z+r_1)^2}\right]. \quad (1)$$

where $\epsilon$ is a thermal expansion factor of the sub. $\epsilon$ was put into the equation to verify that the field cancellation by the bucking magnets also works if thermal expansion of the subs is taken into account.

The flux due to the first bucking magnet is:

$$B_{b1}(z) = \frac{\Phi_{b1}}{4\pi\varepsilon^2}\left[\frac{1}{\left[z-\left(r_{b1}-\frac{d_1}{2}\right)\right]^2} - \frac{1}{\left[z-\left(r_{b1}+\frac{d_1}{2}\right)\right]^2}\right], \quad (2)$$

the flux due to the second bucking magnet is:

$$B_{b2}(z) = \frac{\Phi_{b2}}{4\pi\varepsilon^2}\left[\frac{1}{\left[z-\left(r_{b2}-\frac{d_{21}}{2}\right)\right]^2} - \frac{1}{\left[z-\left(r_{b2}+\frac{d_{21}}{2}\right)\right]^2}\right]. \quad (3)$$

Figure 5:
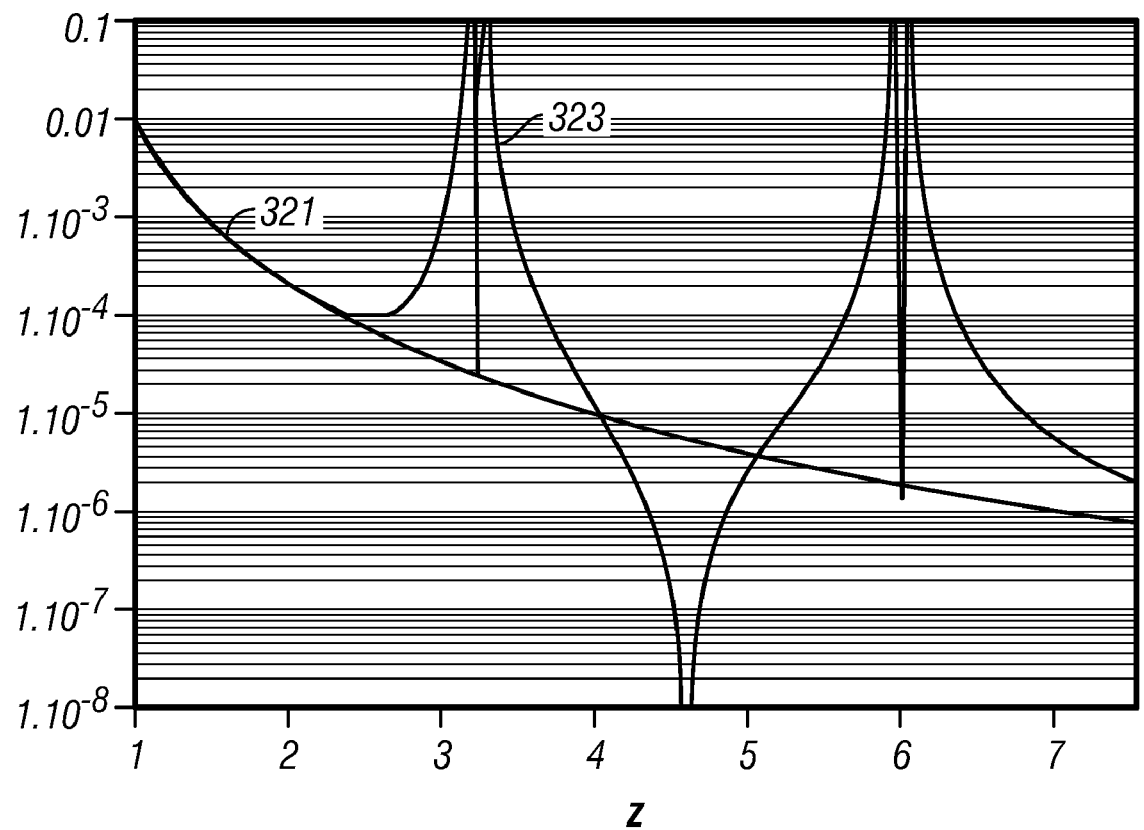
FIG. 5 shows the magnetic field for the magnet arrangement of FIG. 3.

FIG. 5 shows the flux due to the NMR magnets 321 and the resulting field 323 with the NMR magnets and the two bucking magnets. The abscissa is the distance from the midpoint of the NMR magnets. Based on this simulation, the magnetometer should be positioned at a distance $z_0$ of about 4.6 m from the NMR sensor center where there is a minimum of the total field (less than 10 nT in this example).

The particular structure illustrated in FIG. 3 was based on the following principles. It is desirable to get a range of locations (as opposed to a sharp location) where the B field vanishes. This requires two conditions to be fulfilled:

1. The field of the correction magnet(s) needs to oppose the NMR-Sensor field at the location of the magnetic directional sensor; and 2. The B gradient of the NMR sensor needs to be matched by a negative gradient of the same magnitude from the bucking magnet(s).

If one uses only one bucking magnet, this magnet must be quite long to fulfill the second requirement. In addition, the location where both conditions are met (the position of the magnetic sensor) is quite a long distance away from the NMR Sensor magnets.

Those skilled in the art would recognize that the first bucking magnet must be between NMR-Sensor and the magnetic directional sensor because it is the only way to satisfy the second requirement above. For a first bucking magnet of reasonable length it turns out that if B is canceled, the B gradient is not quite matched. This can be achieved by using a second bucking magnet on the other side of the magnetic directional sensor.

The present invention, in another aspect, provides a method of using the apparatus of present invention in a borehole environment. The method relates to assembly and calibration of a downhole sub that includes a NMR sensor as discussed above. Accordingly, in one embodiment of the invention, prior to lowering the tool into the wellbore, the positioning of the components of the apparatus of FIG. 3 is adjusted so that the magnetometer measurements are within acceptable tolerances. This positioning may be done either at the factory or may be done at the wellsite.

During calibration, the sub containing the magnetometer is first clamped in a near vertical position (without the NMR sensor) using a clamping device which is rotatable. Magnetometer measurements (a first set) are made at a plurality of known orientations of the sub without the presence of any disturbance caused by the NMR sensor. This may be done by using a stepper motor. The measurements of the magnetometer at the plurality of known orientations are recorded. Next, the NMR sensor assembly is added to the sub and the compensating magnets are positioned straddling the magnetometer. The magnetometer measurements are then repeated at the plurality of the known orientations of the sub and compared to the first set of measurements made without the NMR sensor and the compensating magnets. If the new measurements are within acceptable tolerance, then the sub is suitable for use downhole. If the new measurements are not within acceptable tolerance of the first measurements, then the position of the compensating magnets is adjusted, such as by using positioning screws. The process described above may be repeated until the magnetometer measurements are within the acceptable tolerance.

By using the method and apparatus disclosed above, the correct azimuthal direction may be associated with directionally sensitive measurements made by a formation evaluation sensor. The formation evaluation sensor may be a nuclear sensor (such as a gamma-ray density or a neutron porosity sensor), a resistivity sensor, and/or an acoustic sensors. These types of sensors are mentioned only as examples of directionally sensitive formation evaluation sensors. In addition, correct magnetometer measurements may be used for surveying the borehole position and orientation. With the use of the present disclosure, these directionally sensitive measurements may be stored on a suitable medium or displayed. Additional drilling or completion operations may be carried out on the basis of the correctly oriented measurements.

The description above has been in terms of a device conveyed on a BHA on a drilling tubular into a borehole in the earth formation. The method and apparatus described above could also be used in conjunction with a logging string conveyed on a wireline into the earth formation. For the purposes of the present disclosure, the BHA and the logging string may be referred to as a "downhole assembly."

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. An apparatus configured to correct for an effect of a source of a magnetic disturbance on a downhole assembly conveyed in a borehole in the earth formation, the apparatus comprising:
at least one magnet on the downhole assembly configured to produce a magnetic field at a selected location on the downhole assembly that substantially cancels a magnetic field produced by the source of the magnetic disturbance, the at least one magnet not being part of a nuclear magnetic resonance sensor and further configured so that a gradient of the magnetic field produced by the at least one magnet substantially cancels a gradient of the magnetic field produced by the source of the disturbance.

2. The apparatus of claim 1 wherein the at least one magnet further comprises a pair of magnets disposed on opposite sides of the selected location, each of the pair of magnets having a similar orientation.

3. The apparatus of claim 1 wherein the source of the magnetic disturbance further comprises a magnet of a nuclear magnetic resonance (NMR) sensor, the magnet of the NMR sensor being made of substantially the same material as a material of the at least one magnet.

4. The apparatus of claim 1 wherein the material of the at least one magnet is selected to maintain the cancellation of the field produced by the source of magnetic disturbance when a temperature of the downhole assembly changes.

5. The apparatus of claim 1 wherein the downhole assembly is selected from (i) a bottomhole assembly conveyed on a drilling tubular, and (ii) a logging string conveyed on a wireline.

6. A method of correcting for an effect of a source of a magnetic disturbance on a downhole assembly conveyed in a borehole in the earth formation, the method comprising:
positioning at least one magnet that is not part of a nuclear magnetic resonance sensor on the downhole assembly to produce a magnetic field at the selected location that, at a selected location:
(A) substantially cancels a magnetic field produced by the source of the magnetic disturbance, and
(B) a gradient of the magnetic field produced by the at least one magnet substantially cancels a gradient of the magnetic field produced by the source of the disturbance.

7. The method of claim 6 wherein positioning the at least one magnet further comprises positioning a pair of magnets on opposite sides of the selected location, each of the pair of magnets having a similar orientation.

8. The method of claim 6 wherein the source of the magnetic disturbance further comprises a magnet of a nuclear magnetic resonance (NMR) sensor, the method further comprising using a material for the at least one magnet that is substantially the same as the magnet of the NMR sensor.

9. The method of claim 6 wherein the downhole assembly further comprises a logging string, the method further comprising conveying the logging string into the borehole on a wireline.

10. The method of claim 6 wherein the downhole assembly further comprises a bottomhole assembly (BHA), the method further comprising conveying the BHA into the borehole on a drilling tubular.

11. The apparatus of claim 1 further comprising:
(i) a magnetometer on the downhole assembly configured to provide a measurement indicative of an orientation of the downhole assembly, the measurement being subject to the magnetic disturbance;
(ii) a formation evaluation (FE) sensor on the downhole assembly configured to provide an FE measurement indicative of a property of the formation; and
(iii) a processor configured to associate an orientation angle with the FE measurement using the output of the magnetometer.

12. The apparatus of claim 11 wherein the at least one magnet further comprises a pair of magnets disposed on opposite sides of the selected location, each of the pair of magnets having a similar orientation.

13. The apparatus of claim 11 wherein the source of the magnetic disturbance further comprises a magnet of a nuclear magnetic resonance (NMR) sensor, the magnet of the NMR sensor being made of substantially the same material as a material of the at least one magnet.

14. The apparatus of claim 11 wherein a material of the at least one magnet is selected to maintain the cancellation in the presence of a temperature change of the downhole assembly.

15. The apparatus of claim 11 wherein the downhole assembly is selected from (i) a bottomhole assembly conveyed on a drilling tubular, and (ii) a logging string conveyed on a wireline.

16. The apparatus of claim 11 wherein the processor is further configured to at least one of: (i) store the FE measurement and the associated orientation on a suitable medium, and (ii) display the FE measurement and the associated orientation.

17. The apparatus of claim 11 wherein the FE sensor is selected from the group consisting of (i) a resistivity sensor, (ii) an acoustic sensor, (iii) a density sensor, and (iv) a porosity sensor.

18. The apparatus of claim 11 wherein the processor is further configured to provide an orientation angle of the downhole assembly.

19. The method of claim 6 further comprising:
(i) using a magnetometer on the downhole assembly to provide a measurement indicative of an orientation of the downhole assembly, the measurement being subject to the magnetic disturbance;
(ii) making a formation evaluation (FE) measurement indicative of a property of the formation; and
(iii) associating an orientation angle with the FE measurement using the output of the magnetometer.

20. The method of claim 19 further comprising using for the at least one magnet a pair of magnets disposed on opposite sides of the magnetometer, each of the pair of magnets having a similar orientation.

21. The method of claim 19 further comprising using as the source of the magnetic disturbance a magnet of a nuclear magnetic resonance (NMR) sensor, method further comprising making the magnet of the NMR sensor of substantially the same material as a material of the at least one magnet.

22. The method of claim 19 further comprising conveying the downhole assembly on one of: (i) a drilling tubular, and (ii) a wireline.

23. The method of claim 19 further comprising at least one of: (i) storing the FE measurement and the associated orientation on a suitable medium, and (ii) displaying the FE measurement and the associated orientation.

24. The method of claim 19 further comprising using as the FE sensor at least one of: (i) a resistivity sensor, (ii) an acoustic sensor, (iii) a density sensor, and (iv) a porosity sensor.

25. The apparatus of claim 19 wherein the processor is further configured to provide an orientation angle of the downhole assembly.

* * * * *